(12) United States Patent
Nakagawa et al.

(10) Patent No.: US 10,878,563 B2
(45) Date of Patent: Dec. 29, 2020

(54) THREE-DIMENSIONAL SHAPE DATA PRODUCTION METHOD AND THREE-DIMENSIONAL SHAPE DATA PRODUCTION SYSTEM

(71) Applicants: RION Co., Ltd., Tokyo (JP); Utsunomiya University, Tochigi (JP)

(72) Inventors: Takeshi Nakagawa, Tokyo (JP); Daisuke Barada, Tochigi (JP)

(73) Assignees: RION Co., Ltd., Tokyo (JP); Utsunomiya University, Tochigi (JP)

( * ) Notice: Subject to any disclaimer, the term of this patent is extended or adjusted under 35 U.S.C. 154(b) by 48 days.

(21) Appl. No.: 16/288,466

(22) Filed: Feb. 28, 2019

(65) Prior Publication Data

US 2019/0272633 A1 Sep. 5, 2019

(30) Foreign Application Priority Data

Mar. 5, 2018 (JP) .................................. 2018-039011
Feb. 26, 2019 (JP) .................................. 2019-032814

(51) Int. Cl.
| | | |
|---|---|---|
| *G06K 9/00* | (2006.01) | |
| *G06T 7/00* | (2017.01) | |
| *H04R 25/00* | (2006.01) | |
| *H04R 1/10* | (2006.01) | |
| *H04R 25/02* | (2006.01) | |

(52) U.S. Cl.
CPC .......... *G06T 7/0012* (2013.01); *H04R 1/1016* (2013.01); *H04R 25/02* (2013.01); *H04R 25/652* (2013.01); *G06T 2207/30004* (2013.01)

(58) Field of Classification Search
CPC combination set(s) only.
See application file for complete search history.

(56) References Cited

U.S. PATENT DOCUMENTS 8,150,162 B2 * 4/2012 Du ........................ G06K 9/224
382/181
2015/0190043 A1* 7/2015 Hatzilias ................ A61B 1/227
600/111

FOREIGN PATENT DOCUMENTS

JP 2000210327 A 8/2000

\* cited by examiner

*Primary Examiner* — Alex Kok S Liew
(74) *Attorney, Agent, or Firm* — Rankin, Hill & Clark LLP

(57) ABSTRACT

A three-dimensional shape data production method and a system for the same for realizing contactless receiving of data regarding the inner shape of a tubular body which includes a step of generating multiple pieces of two-dimensional image data based on a signal from an image capturing device configured to be movable inside a tubular body and configured to capture an image of the inside of the tubular body; a step of receiving space information on the image capturing device upon image capturing by the image capturing device based on a signal from a motion sensor placed at the image capturing device; and a step of associating the two-dimensional image data and the space information with each other and generating three-dimensional shape data of the inside of the tubular body based on the two-dimensional image data and the space information.

5 Claims, 6 Drawing Sheets

EXTERNAL EAR CANAL

TWO-DIMENSIONAL IMAGE DATA GENERATOR 30
SPACE INFORMATION RECEIVER 31
THREE-DIMENSIONAL SHAPE DATA GENERATOR 32

EXTERNAL EAR CANAL

TWO-DIMENSIONAL IMAGE DATA GENERATOR 30
SPACE INFORMATION RECEIVER 31
THREE-DIMENSIONAL SHAPE DATA GENERATOR 32

THREE-DIMENSIONAL SHAPE DATA PRODUCTION METHOD AND THREE-DIMENSIONAL SHAPE DATA PRODUCTION SYSTEM

CROSS-REFERENCE TO RELATED APPLICATION

This application claims priorities from Japanese Patent Applications 2018-039011 and 2019-032814, respectively filed with the Japan Patent Office on Mar. 5, 2018 and on Feb. 26, 2019, the entire content of which is hereby incorporated by reference.

BACKGROUND

1. Technical Field

The present disclosure relates to a three-dimensional shape data production method and a three-dimensional shape data production system. Specifically, the present disclosure relates to the method for realizing contactless receiving of the three-dimensional shape of the inside of a tubular body such as an external ear canal and reproduction of such a received shape and a system for such a method.

2. Related Art

A hearing aid is used with being inserted into the external ear canal of a user thereof. Thus, a custom in-the ear type hearing aid and an ear mold produced in accordance with the shape of the external ear canal of the user have been known. For example, for making an ear impression, data regarding the inner shape of the external ear canal of the user needs to be collected. Thus, in a typical case, an impression material is injected into the external ear canal with a syringe, and then, is hardened. Then, the ear impression making process of taking out the hardened impression material to make the ear impression of the user is performed (see, e.g., JP-A-2000-210327).

In the ear impression making process, in a case where the curvature of the external ear canal is, for example, sharp, the hardened impression material cannot be sometimes taken out. An elderly person has the sagging skin of the external ear canal, i.e., wrinkles. In this case, when the impression material is injected, the skin moves due to the injected impression material, and for this reason, the ear impression having been formed is different from an original shape. Moreover, the accuracy of the ear impression depends on the skill of a person making the ear impression. For this reason, different persons making the ear impression might make different ear impression shapes. Thus, the technique of receiving data on the inner shape of the external ear canal without use of the impression material has been demanded.

Meanwhile, the technique of performing contactless measurement of an object shape has advanced in recent years. However, such a measurement technique is often for measuring an outer shape of the object. Thus, the technique of receiving data on the three-dimensional shape of the inside of a tubular body such as the external ear canal is not a general technique.

The present disclosure is intended to solve these problems. That is, the present disclosure is intended to provide a three-dimensional shape data production method and a three-dimensional shape data production system for realizing contactless receiving of data regarding the inner shape of a tubular body such as an external ear canal and reproduction of such data.

SUMMARY

A three-dimensional shape data production method as one aspect of the present disclosure includes the step of generating two-dimensional image data based on a signal from an image capturing device configured to be movable inside a tubular body and configured to capture an image of the inside of the tubular body, the step of receiving space information on the image capturing device upon image capturing by the image capturing device based on a signal from a motion sensor, and the step of associating the two-dimensional image data and the space information with each other and generating three-dimensional shape data of the inside of the tubular body based on the two-dimensional image data and the space information.

DETAILED DESCRIPTION

Figure 1A:
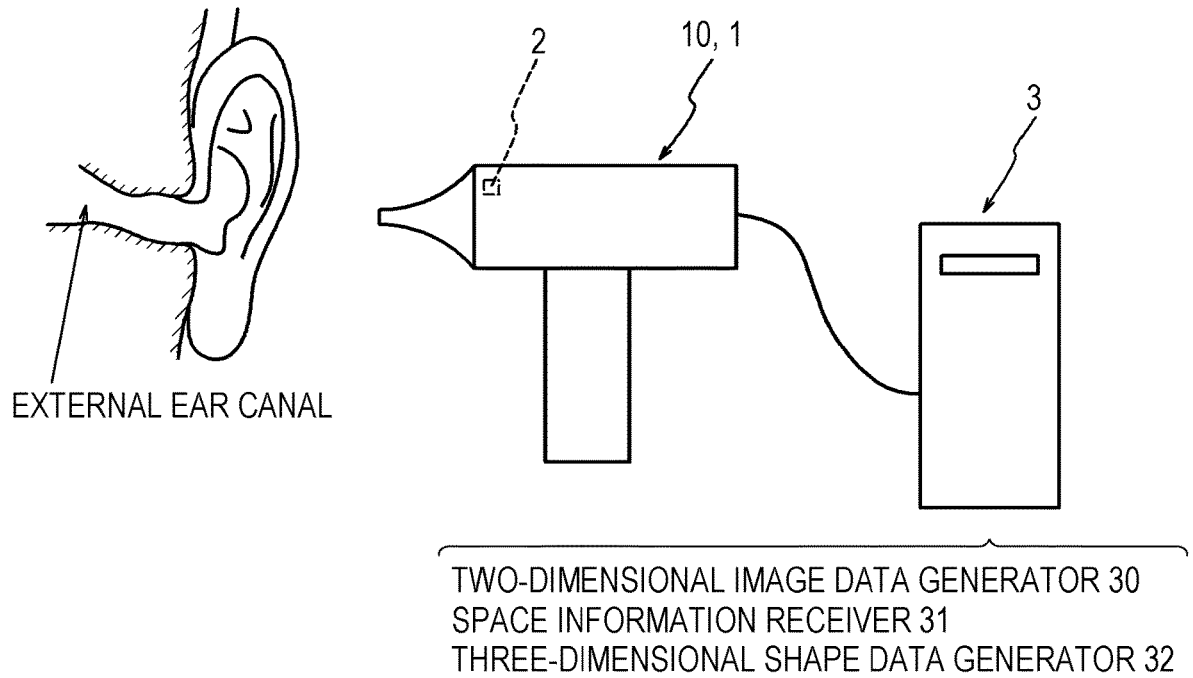
FIGS. 1A and 1B are schematic views of one embodiment of a three-dimensional shape data production system according to the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

A three-dimensional shape data production method of an embodiment according to the present disclosure includes a step of generating multiple pieces of two-dimensional image data based on a signal from an image capturing device configured to be movable inside a tubular body and configured to capture an image of the inside of the tubular body; a step of receiving space information on the image capturing device upon image capturing by the image capturing device based on a signal from a motion sensor placed at the image capturing device; and a step of relating the two-dimensional image data and the space information with each other and generating three-dimensional shape data of the inside of the tubular body based on the two-dimensional image data and the space information.

In the three-dimensional shape data production method, the image capturing device includes a lighting, an objective optical system, and an image capturing element having multiple light receiving elements arranged at a position of image formation by the objective optical system and configured to receive reflected light from the inside of the tubular body, the step of generating the three-dimensional shape data includes a step of calculating a movement locus of a principal point of the objective optical system in association with movement of the image capturing device based on the space information to set cylindrical coordinates about the movement locus as a center axis and discretizing a surrounding space of the image capturing device based on the cylindrical coordinates to set that the surrounding space is formed with multiple infinitesimal surfaces according to the cylindrical coordinates, a step of setting a straight line connecting each light receiving element of the image capturing element and the principal point, a step of determining whether or not the infinitesimal surfaces exist on the straight line, a step of determining, when it is determined that the infinitesimal surfaces exist on the straight line, whether or not reflected light from the infinitesimal surfaces can enter each light receiving element of the image capturing element, a step of setting a pixel value of each pixel of the two-dimensional image data as a sum of an intensity of the reflected light from each of the infinitesimal surfaces and calculating the intensity of the reflected light on each of the infinitesimal surfaces exists on the straight line based on the pixel value, and a step of estimating the infinitesimal surfaces inside an actual tubular body based on distribution of the reflected light intensity of each of the infinitesimal surfaces exists on the straight line and building three-dimensional shape data of the inside of the tubular body based on the estimated infinitesimal surfaces.

In the three-dimensional shape data production method e image capturing device includes an lighting, an objective optical system, and an image capturing element arranged at a position of image formation by the objective optical system and configured to receive reflected light from the inside of the tubular body, the step of generating the three-dimensional shape data includes a step of receiving, in advance, reference data regarding a pixel value corresponding to a distance between a principal point of the objective optical system and the inside of the tubular body, a step of calculating a movement locus of the principal point of the objective optical system in association with movement of the image capturing device based on the space information to set cylindrical coordinates about the movement locus as a center axis and setting a cylinder having a predetermined radius and including multiple infinitesimal surfaces according to the cylindrical coordinates, a step of setting a straight line connecting each light receiving element of the image capturing element and the principal point, a step of determining whether or not the infinitesimal surfaces exist on the straight line, a step of extracting the infinitesimal surfaces corresponding to the two-dimensional image data, a step of obtaining a distance between the principal point at a position receiving the two-dimensional image data and the infinitesimal surface from a pixel value corresponding to each extracted infinitesimal surface based on the reference data, and a step of calculating a tubular body shape according to the distance.

The three-dimensional shape data production method may further include a step of correcting the space information on the image capturing device as obtained by the motion sensor based on the space information on the tubular body upon image capturing, the space information on the tubular body being obtained by other motion sensors.

A three-dimensional shape data production system of another embodiment according to the present disclosure includes a two-dimensional image data generation device configured to generate multiple pieces of two-dimensional image data based on a signal from an image capturing device configured to be movable inside a tubular body and configured to capture an image of the inside of the tubular body; a space information receiving device configured to receive space information on the image capturing device upon image capturing based on a signal from a motion sensor placed at the image capturing device; and a three-dimensional shape data generation device configured to relate the two-dimensional image data and the space information with each other and generate three-dimensional shape data of the inside of the tubular body based on the two-dimensional image data and the space information.

In the three-dimensional shape data production system, the image capturing device includes a lighting, a tip end portion having an objective optical system into which reflected light from the inside of the tubular body which radiates at the lighting enters, a bent portion supporting the tip end portion and provided bendably, and an image capturing element arranged at a position of image formation by the objective optical system and configured to receive reflected light from the inside of tubular body, and the motion sensor is preferably provided at the tip end portion.

The three-dimensional shape data production system further comprises a storage device configured to receive and store, in advance, reference data regarding a pixel value corresponding to a distance between a principal point of the objective optical system and the inside of the tubular body, and the three-dimensional shape data generation device calculates a movement locus of the principal point of the objective optical system in association with movement of the image capturing device based on the space information to set cylindrical coordinates having the movement locus as a center axis, sets a cylinder having a predetermined radius and including multiple infinitesimal surfaces according to the cylindrical coordinates, and sets a straight line connecting each light receiving element of an image capturing element and the principal point, determines whether or not the infinitesimal surfaces exist on the straight line, extracts the infinitesimal surfaces corresponding to the two-dimensional image data, and obtains a distance between the principal point at a position receiving the two-dimensional image data and the infinitesimal surface from a pixel value corresponding to each extracted infinitesimal surface based on the reference data.

Moreover, a holding device configured to directly or indirectly hold the tubular body is preferably further provided.

According to the method or the system of the present disclosure, the three-dimensional shape data of the inside of the tubular body can be generated from the multiple pieces of the two-dimensional image data of the inside of the tubular body obtained by the image capturing device and the space information on the image capturing device as obtained by the motion sensor. That is, contactless receiving and reproduction of data regarding the inner shape of the tubular body can be realized. Thus, a problem when an ear impression is made using an impression material can be solved in such a manner that the three-dimensional shape data of the inside of the external ear canal is generated by the method or the system according to the present disclosure.

Hereinafter, a three-dimensional shape data production method and a three-dimensional shape data production system for the inside of a tubular body according to one embodiment of the present disclosure will be described with reference to the drawings. Note that in the present embodiment, the case of producing three-dimensional shape data of an external ear canal will be described as one example.

Figure 1B:
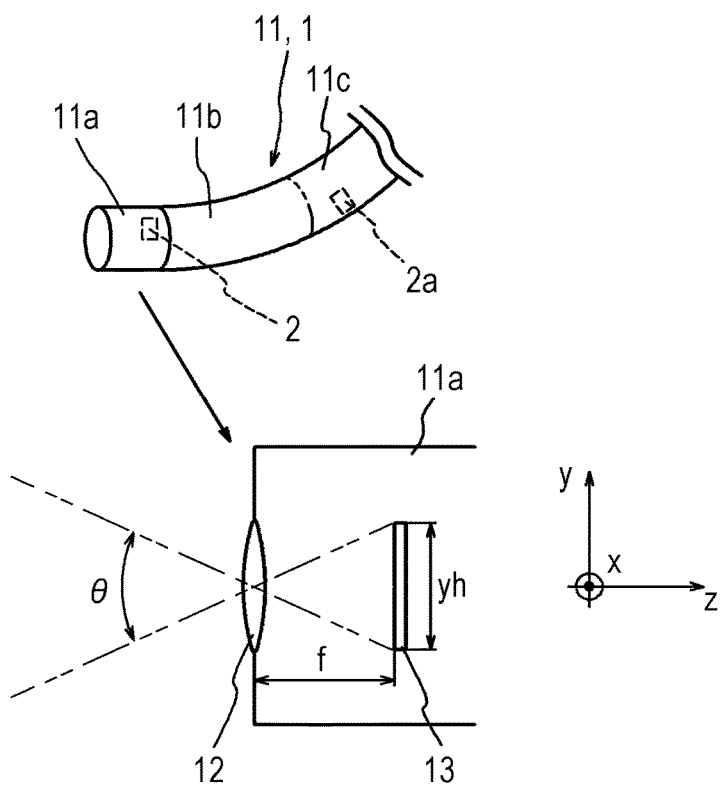

As illustrated in FIGS. 1A and 1B, the three-dimensional shape data production system of the present embodiment includes an image capturing device 1, a motion sensor 2, and a computer 3.

The image capturing device 1 is movable inside the external ear canal of a human body, and is configured to capture an image of the inside of the external ear canal. Such a device includes, for example, an otoscope 10 illustrated in FIG. 1A and a video scope 11 illustrated in FIG. 1B. The video scope 11 includes an objective optical system 12 and an image capturing element 13 at an end portion on a side to be inserted into the external ear canal. Note that although not shown in the figure, a fiberscope may be employed as the image capturing device 1. The fiberscope includes an objective optical system at an end portion on a side to be inserted into the external ear canal. Light having entered through the objective optical system is guided by a fiber cable. An image capturing element arranged at an opposite end portion of the fiberscope is configured to convert the light from the objective optical system into an electric signal.

Figure 2:
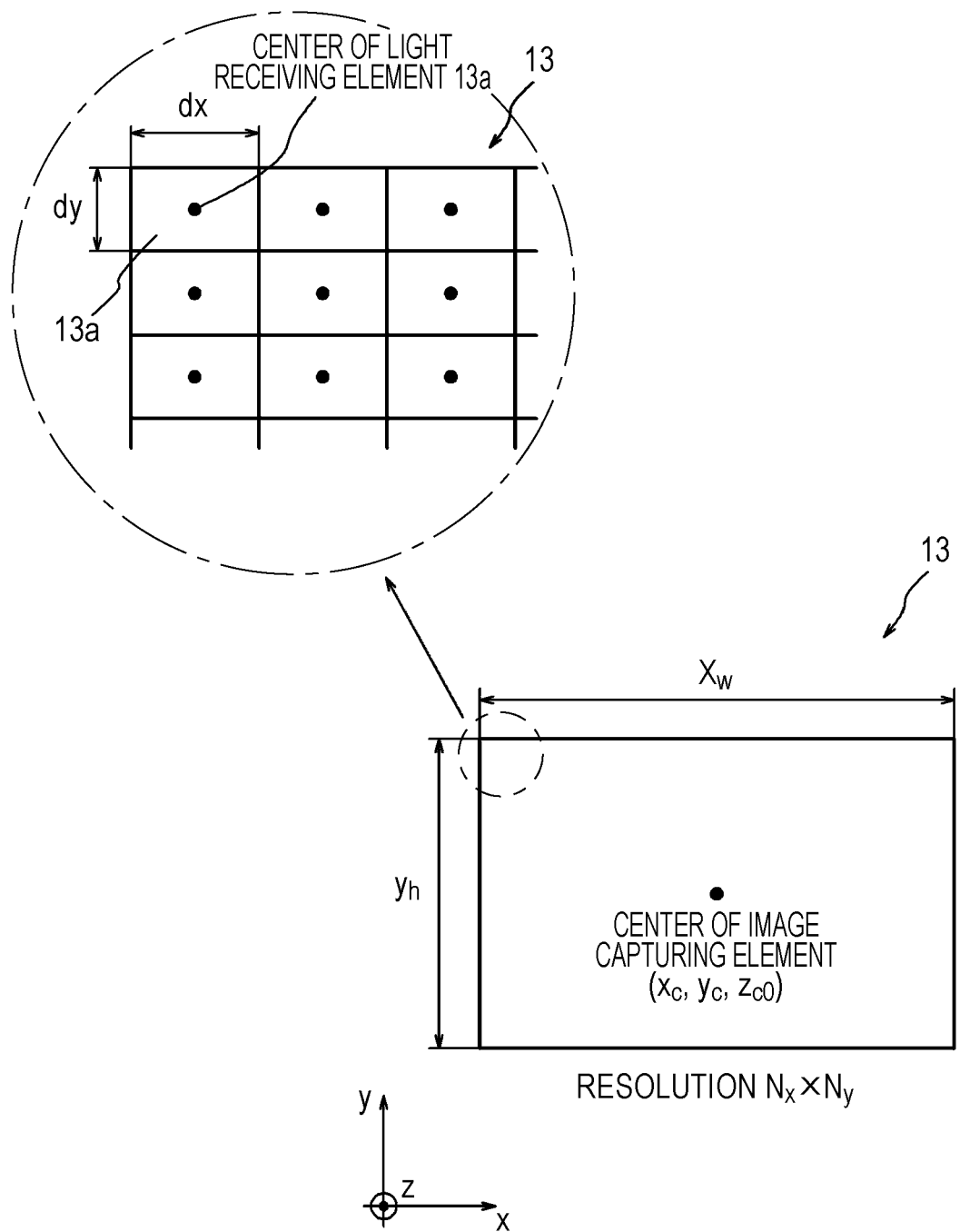
FIG. 2 is a view of one embodiment of an image capturing element.

As illustrated in FIG. 1B, the image capturing device 1 includes the objective optical system 12. The objective optical system 12 may include a single lens. Alternatively, multiple lenses may be combined. The image capturing element 13 is arranged at an image formation position of the objective optical system 12. The image capturing element 13 is configured to receive, from the inside of the external ear canal, reflected light having entered into the external ear canal from the objective optical system 12, thereby converting the light into an electric signal. As illustrated in FIG. 2, the image capturing element 13 includes multiple light receiving elements 13a. Note that although not shown in the figure, the image capturing device 1 includes a lighting device configured to irradiate an object targeted for image capturing with light. Thus, favorable image capturing can be performed even for the inside of the external ear canal into which light is less enterable from the outside.

The motion sensor 2 is configured to receive space information on the image capturing device 1, i.e., information regarding the position and posture of the image capturing device 1. Specifically, the motion sensor 2 includes a triaxial acceleration sensor and a triaxial angular velocity sensor. Thus, the position and posture of the image capturing device 1 in orthogonal coordinates can be detected. Note that in a case where the image capturing device 1 is restricted to move only in a uniaxial direction with a certain posture, the space information on the image capturing device 1 as sensed by the motion sensor 2 may be only the position in the uniaxial direction. Considering available positions and postures of the image capturing device 1, various motion sensors 2 can be selected.

The motion sensor 2 is preferably provided at such a location that the position and the posture with respect to the objective optical system 12 and the image capturing element 13 of the image capturing device 1 are not changeable. For example, in the case of providing the motion sensor 2 at the otoscope 10, the motion sensor 2 may be at a location close to a portion to be inserted into the external ear canal as illustrated in FIG. 1A. Alternatively, the motion sensor 2 may be at an opposite location. In a case where the video scope 11 includes, as illustrated in FIG. 1B, a tip end portion 11a having the objective optical system 12 and the image capturing element 13 and a bent portion 11b supporting the tip end portion 11a and provided bendably, the motion sensor 2 is preferably provided at the tip end portion 11a. This is because the positions and postures of the motion sensor 2, the objective optical system 12 and the image capturing element 13 are not changeable. Note that in the case of providing the motion sensor 2 at the tip end portion 11a, another motion sensor 2a may be provided at an outer portion 11c. The outer portion 11c is a portion of the bent portion 11b positioned outside the external ear canal when the video scope 11 is inserted into the external ear canal. In the case of providing these multiple motion sensors, if the motion sensor 2a includes a three-dimensional angular velocity sensor, the posture of the motion sensor 2 can be estimated from information from such a sensor. In the case of using the multiple motion sensors as described above, the three-dimensional angular velocity sensor is not necessarily provided at the motion sensor 2 to be provided at the tip end portion 11a. Note that in the case of providing the motion sensor 2 at the fiberscope, the motion sensor is preferably provided at a tip end portion provided with the objective optical system.

The computer 3 is connected to the image capturing device 1 and the motion sensor 2. Moreover, the computer 3 is configured to receive electric signals output from the image capturing device 1 and the motion sensor 2. The computer 3 of the present embodiment functions as a two-dimensional image data generation device 30, a space information receiving device 31, and a three-dimensional shape data generation device 32. As described later, the two-dimensional image data generation device 30 is configured to generate two-dimensional image data of the inside of the external ear canal based on an electric signal output from the image capturing device 1. The electric signal output from the image capturing device 1 is the group of electric signals output from the light receiving elements 13a, and as described later, is converted into a pixel value for each light receiving element. Moreover, the space information receiving device 31 is configured to receive the space information on the image capturing device 1 upon image capturing based on an electric signal output from the motion sensor 2. Further, the three-dimensional shape data generation device 32 is configured to relate the two-dimensional image data generated by the two-dimensional image data generation device 30 and the space information received by the space information receiving device 31 with each other. In addition, the three-dimensional shape data generation device 32 is configured to generate three-dimensional shape data of the inside of the external ear canal based on the two-dimensional image data and the space information related with each other. Note that although not shown in the figure, various types of peripheral equipment including, e.g., an input device configured to input data to the computer 3, such as a mouse and a keyboard, and an output device configured to output data processed by the computer 3, such as a monitor and a printer, can be connected to the computer 3.

Note that although not shown in the figure, the three-dimensional shape data production system of the present embodiment may include an external ear canal motion sensor different from the motion sensor 2. The external ear canal motion sensor is configured to receive space information on the external ear canal. The external ear canal motion sensor is not necessarily directly attached to the inside of the external ear canal as long as the external ear canal motion sensor is attached to a portion at which the position and posture of an attachment portion relative to the external ear canal are not changeable, such as the head of a person targeted for image capturing. When the person targeted for image capturing moves during image capturing, the space information on the image capturing device 1 as obtained by the motion sensor 2 changes although the relative positions and postures of the image capturing device 1 with respect to the external ear canal are not changeable. However, in the case of providing the external ear canal motion sensor, such a change amount of the position and posture of the external ear canal is obtained. Thus, the space information on the image capturing device 1 as obtained by the motion sensor 2 can be corrected based on such a change amount. That is, for the obtained space information, influence of motion of the person targeted for image capturing can be eliminated. Note that instead of the external ear canal motion sensor, a structure for directly or indirectly holding the tubular body such as the external ear canal may be used. Such a structure may be used in combination with the external ear canal motion sensor. Such a structure includes, for example, a chin rest on which the chin of the person targeted for image capturing is placed such that the head is fixed, i.e., the external ear canal is fixed.

Next, the three-dimensional shape data production method by the three-dimensional shape data production system will be described.

First, an area where image capturing by the image capturing element 13 is allowed will be described. As illustrated in FIGS. 1B and 2, in a case where the image capturing element 13 is arranged parallel to a xy plane, the area where image capturing by the image capturing element 13 is allowed is an inner region indicated by chain double-dashed lines in FIG. 1B. As illustrated in the figure, in a case where the width, i.e., the x-direction length, of the image capturing element 13 is xw, the height, i.e., the y-direction length, of the image capturing element 13 is yh, the angle of view and the diagonal angle of view are θ, and a focal length is f, these values are in a relationship of the following formula (Formula 1).

$$f = \frac{\sqrt{x_w^2 + y_h^2}}{2 \tan\frac{\theta}{2}}$$ [Formula 1]

Thus, in generation of the three-dimensional shape data of the inside of the external ear canal, image capturing is performed while the position and posture of the image capturing element 13 are being changed based on the area where image capturing by the image capturing element 13 is allowed. Images of all expected portions are to be captured. An image surface of the image capturing element 13 is within the fiberscope. Thus, in the case of using the fiberscope, the three-dimensional shape data generation device 32 uses the position of the image surface instead of the position of each light receiving element of the image capturing element 13.

As described above, the image capturing element 13 includes the group of the multiple light receiving elements 13a as illustrated in FIG. 2. Light having entered each light receiving element 13a is converted into a voltage value corresponding to the intensity of such light, and such a voltage value is output as an electric signal. The two-dimensional image data generation device 30 converts the output voltage from each light receiving element 13a into a corresponding pixel value, thereby generating a pixel having such a pixel value. This pixel is arranged corresponding to array of the light receiving elements 13a. Thus, the two-dimensional image data generation device 30 generates the two-dimensional image data of the inside of the external ear canal.

Note that x and y positions (xix, yiy) at the center of each light receiving element 13a can be represented as in the following formulae (Formula 2) (Formula 3). For these formulae, the width, i.e., the x-direction length, of the image capturing element 13 is $x_w$, and the height, i.e., the y-direction length, of the image capturing element 13 is $y_h$, as described above. Moreover, the resolution of the image capturing element 13 in an x-direction and the resolution of the image capturing element 13 in a y-direction are Nx and Ny, respectively. Further, the pitch of each light receiving element 13a in the x-direction and the pitch of the light receiving element 13a in the y-direction are dx and dy, respectively. The coordinates of the center position of the image capturing element 13 is $(x_c, y_c, zc_0)$, and variables ix, iy are used.

$$dx = \frac{x_w}{N_x}, \, dy = \frac{y_h}{N_y}$$ [Formula 2]

$$x_{i_x} = \left(i_x + \frac{1-N_x}{2}\right)dx + x_c \, (0 \le i_x \le N_x - 1)$$ [Formula 3]

$$y_{i_y} = \left(i_y + \frac{1-N_y}{2}\right)dx + y_c \, (0 \le i_y \le N_y - 1)$$

The space information receiving device 31 receives the space information on the image capturing device 1 upon image capturing based on an electric signal output from the motion sensor 2. Specifically, after the electric signal has been output from the motion sensor 2, the electric signal of the motion sensor 2 is caught at the timing of performing image capturing by the image capturing device 1. In this manner, the space information on the image capturing device 1 is received. Note that in the case of not receiving the space information, the electric signal from the motion sensor 2 may be stopped, and on the other hand, may be output from the motion sensor 2 with using, as a trigger, an electric signal output upon image capturing by the image capturing device 1.

The two-dimensional image data of the inside of the external ear canal and the space information on the image capturing device 1 as obtained in the above-described manner are related with each other by the three-dimensional shape data generation device 32. Thus, it becomes evident that which parts inside an external ear canal correspond to the obtained two-dimensional image.

Further, the three-dimensional shape data generation device 32 generates the three-dimensional shape data of the inside of the external ear canal based on the two-dimensional image data and the space information related with each other. Specifically, such generation is performed according to the following steps.

First, the image capturing device 1 is moved to an external ear canal portion where three-dimensional shape data is necessary, and the two-dimensional image data and the space information are received at a predetermined interval (e.g., 0.1 mm). The received two-dimensional image data and the received space information are stored in a memory (not-shown) built in the computer 3. Based on the received space information, the movement locus of a principal point of the objective optical system 12 in association with movement of the image capturing device 1 is calculated. Cylindrical coordinates about the movement locus as a center axis are set, assuming that the external ear canal is the tubular body. Further, based on the set cylindrical coordinates, multiple infinitesimal surfaces are set on an inner surface of the tubular body. The computer 3 has a storage unit (not shown), and saves, in advance, reference pixel value data corresponding to a distance 1 between the principal point and the infinitesimal surface in the case of assuming that the reflection intensity of an inner wall surface of the tubular body is an uniform predetermined value.

Figure 3:
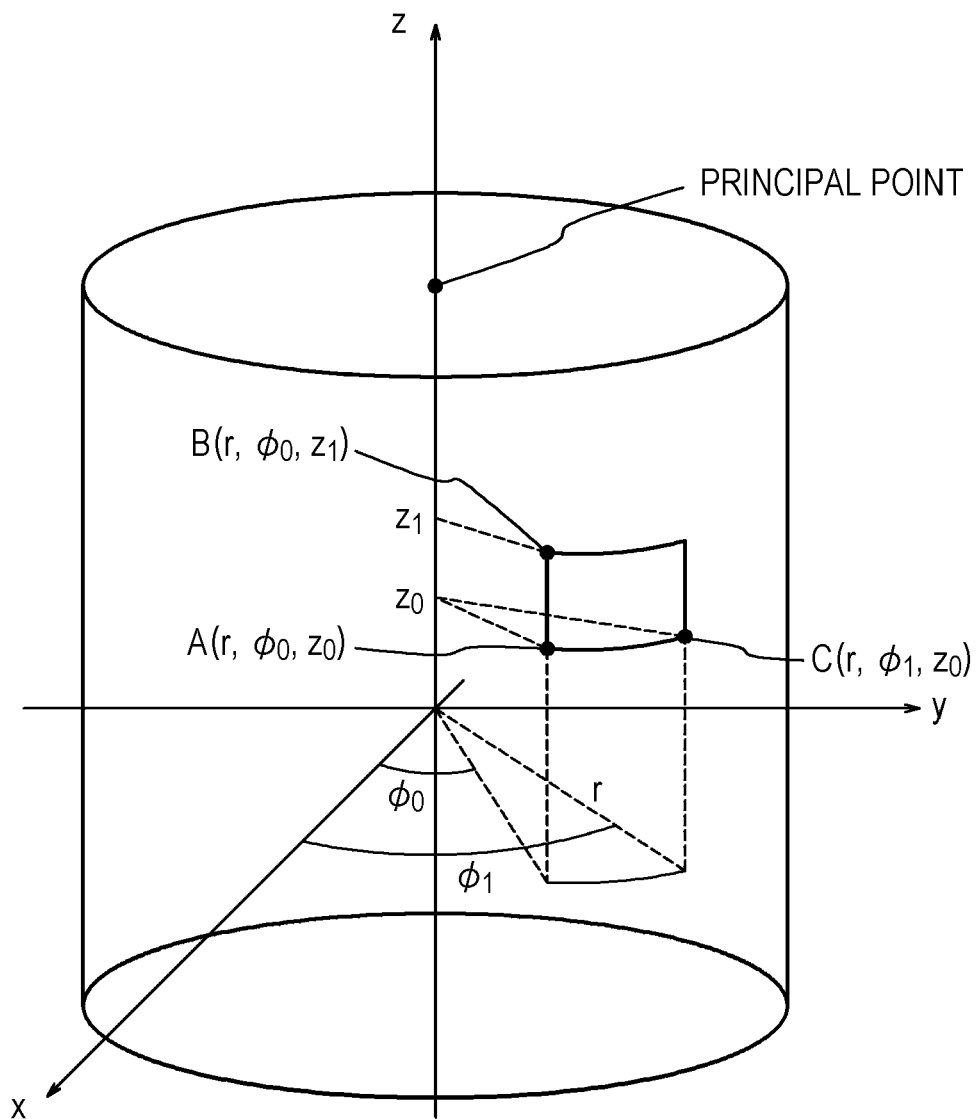
FIG. 3 is a diagram of cylindrical coordinates.

Such setting will be specifically described with reference to the drawings. FIG. 3 illustrates a relationship among the above-described cylindrical coordinates and the multiple infinitesimal surfaces. Note that an external ear canal space is actually in a curved tubular shape, but for the sake of simplicity in concept description, it will be first described that the image capturing device 1 illustrated in FIG. 1B moves along a z-axis of the cylindrical coordinates, i.e., the movement locus of the principal point of the objective optical system 12 is coincident with the z-axis of the cylindrical coordinates. In this state, the cylindrical coordinates about the movement locus of the principal point of the objective optical system 12 as the center axis can be illustrated as in FIG. 3. It is herein assumed that the inner surface of the external ear canal is discretized based on the cylindrical coordinates and a surrounding space is formed by the multiple infinitesimal surfaces defined by the cylindrical coordinates. In this case, these infinitesimal surfaces can be illustrated as rectangular surfaces exist on a cylindrical surface with a certain radius as illustrated in FIG. 3. That is, in FIG. 3, these infinitesimal surfaces are on a cylindrical surface with a radius of $r_0$. The azimuth of one vertex of the infinitesimal surface, such as a point A in FIG. 3, is $\phi_0$, and the z-position of the vertex is $z_0$. In this case, the coordinates of the point A can be represented by ($r_0$, $\phi_0$, $z_0$). Moreover, the coordinates of a vertex present at z1 slightly different from the point A in the z-position, i.e., a point B, can be represented by ($r_0$, $\phi_0$, $z_1$). The coordinates of a vertex present at $\phi_1$ slightly different from the point A in the azimuth, i.e., a point C, can be similarly represented by ($r_0$, $\phi_1$, $z_0$).

In a case where the infinitesimal surface passing through the points A, B, C as illustrated in FIG. 3 is represented using intervening variables $s_1$, $s_2$, such an infinitesimal surface can be represented as in the following formula (Formula 4) by means of parameters $a_{x1}$, $a_{x2}$, $s_{x0}$, $a_{y1}$, $a_{y2}$, $s_{y0}$, $a_{z1}$, $a_{z2}$, $s_{z0}$.

$$x(s_1,s_2)=a_{x1}s_1+a_{x2}s_2+s_{x0}$$

$$y(s_1,s_2)=a_{y1}s_1+a_{y2}s_2+s_{y0}$$

$$z(s_1,s_2)=a_{z1}s_1+a_{z2}s_2+s_{z0} \quad \text{[Formula 4]}$$

The formula (Formula 4) can be represented as in the following formula (Formula 5), provided that the coordinates of the points A, B, C are used, $s_1=0$ and $s_2=0$ are at the point A, $s_1=1$ and $s_2=0$ are at the point B, and $s_1=0$ and $s_2=1$ are at the point C.

$$x(0,0)=r \cos \phi_0$$

$$y(0,0)=r \sin \phi_0$$

$$z(0,0)=z_0$$

$$x(1,0)=r \cos \phi_0$$

$$y(1,0)=r \sin \phi_0$$

$$z(1,0)=z_1$$

$$x(0,1)=r \cos \phi_1$$

$$y(0,1)=r \sin \phi_1$$

$$z(0,1)=z_0 \quad \text{[Formula 5]}$$

By solving the system of simultaneous equations of the above-described formula (Formula 5), the parameters $a_{x1}$, $a_{x2}$, $s_{x0}$, $a_{y1}$, $a_{y2}$, $s_{y0}$, $a_{z1}$, $a_{z2}$, $s_{z0}$ can be obtained.

Figure 4A:
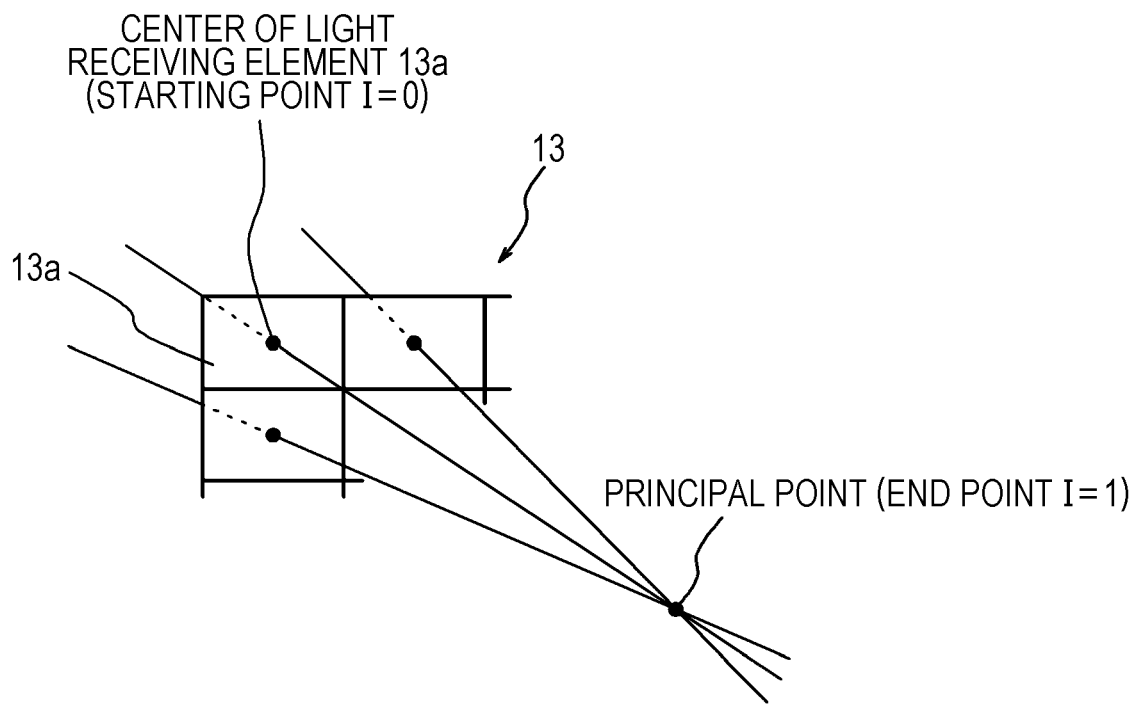
FIGS. 4A and 4B are views for describing a straight line connecting the image capturing element and a principal point of an objective optical system.
Figure 4B:
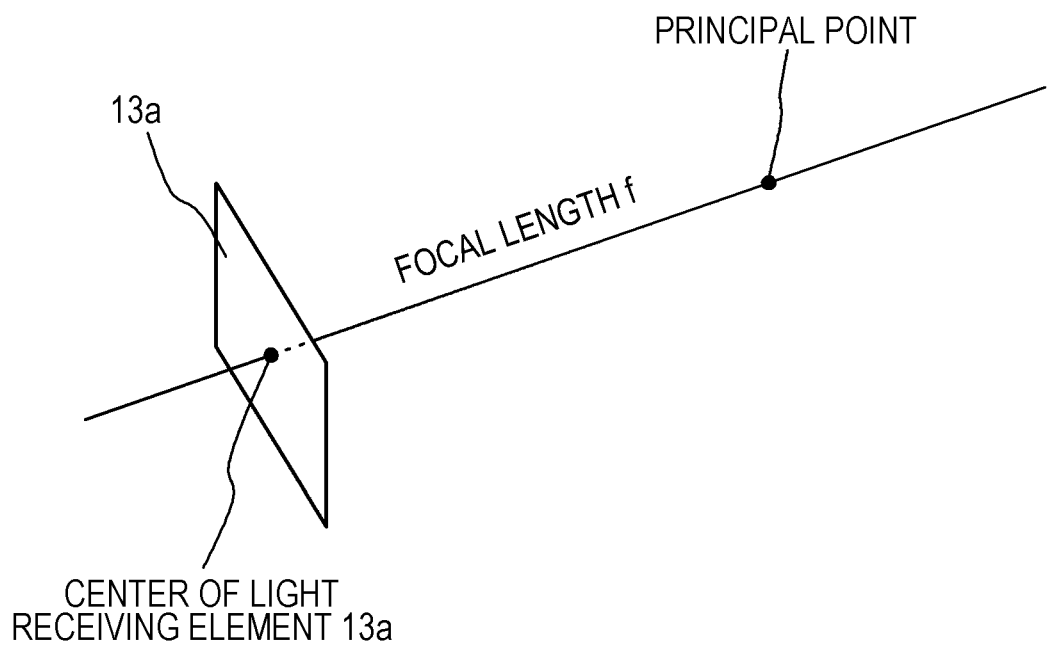

Next, a straight line connecting between the image capturing element 13 and the principal point of the objective optical system 12 is set. The image capturing element 13 in the present embodiment includes the multiple light receiving elements 13a. As illustrated in FIG. 4A, a straight line passing through the center of each light receiving element 13a and the principal point of the objective optical system 12 is set. In the case of representing the straight line by means of an intervening variable 1, the straight line can be represented as in the following formula (Formula 6) by means of parameters $a_x$, $l_{x0}$, $a_y$, $l_{y0}$, $a_z$, $l_{z0}$.

$$x(l)=a_x l+l_{x0}$$

$$y(l)=a_y l+l_{y0}$$

$$z(l)=a_z l+l_{z0} \quad \text{[Formula 6]}$$

It is assumed that coordinates at the center of the light receiving element 13a are ($x_p$, $y_p$, $z_p$) and the coordinates of the principal point of the objective optical system 12 are ($x_f$, $y_f$, $z_f$). In this case, in a case where the straight line passes through the center of the light receiving element 13a and the principal point of the objective optical system 12, the center of the light receiving element 13a is set as a starting point (l=0). Moreover, the principal point of the objective optical system 12 is set as an end point (l=1). In this case, the above-described formula (Formula 6) can be represented as in the following formula (Formula 7).

$$x(0)=x_p$$

$$y(0)=y_p$$

$$z(0)=z_p$$

$$x(1)=x_f$$

$$y(1)=y_f$$

$$z(1)=z_f \quad \text{[Formula 7]}$$

By solving the system of equations of the above-described formula (Formula 7), the parameters $a_x$, $l_{x0}$, $a_y$, $l_{y0}$, $a_z$, $l_{z0}$ can be obtained. Moreover, the straight line passing through the light receiving element 13a and the principal point of the objective optical system 12 can be set.

Next, a correspondence between each light receiving element and each infinitesimal surface is determined. That is, it is determined whether or not the above-described infinitesimal surface exists on the straight line. Specifically, an intersection between a certain plane represented by the formula (Formula 4) and the straight line represented by the formula (Formula 6) is obtained. Then, it is determined whether or not such an intersection is inside the above-described infinitesimal surface and intersects from the inside of the cylinder. That is, in the case of determining that the intersection is inside the infinitesimal surface, it can be regarded that the infinitesimal surface is on the straight line. Conversely, in the case of determining that the intersection is outside the infinitesimal surface, it can be said that the infinitesimal surface does not exist on the straight line. Further, the external ear canal is actually curved, and therefore, a case where the straight line intersects with an external ear canal inner wall again is assumed. Thus, even when multiple infinitesimal surfaces exist on the straight line, only a case where the inner surface faces the image capturing device 1 is taken into consideration. Thus, the infinitesimal surfaces whose images are captured by the image capturing device 1 can be identified.

Figure 5:
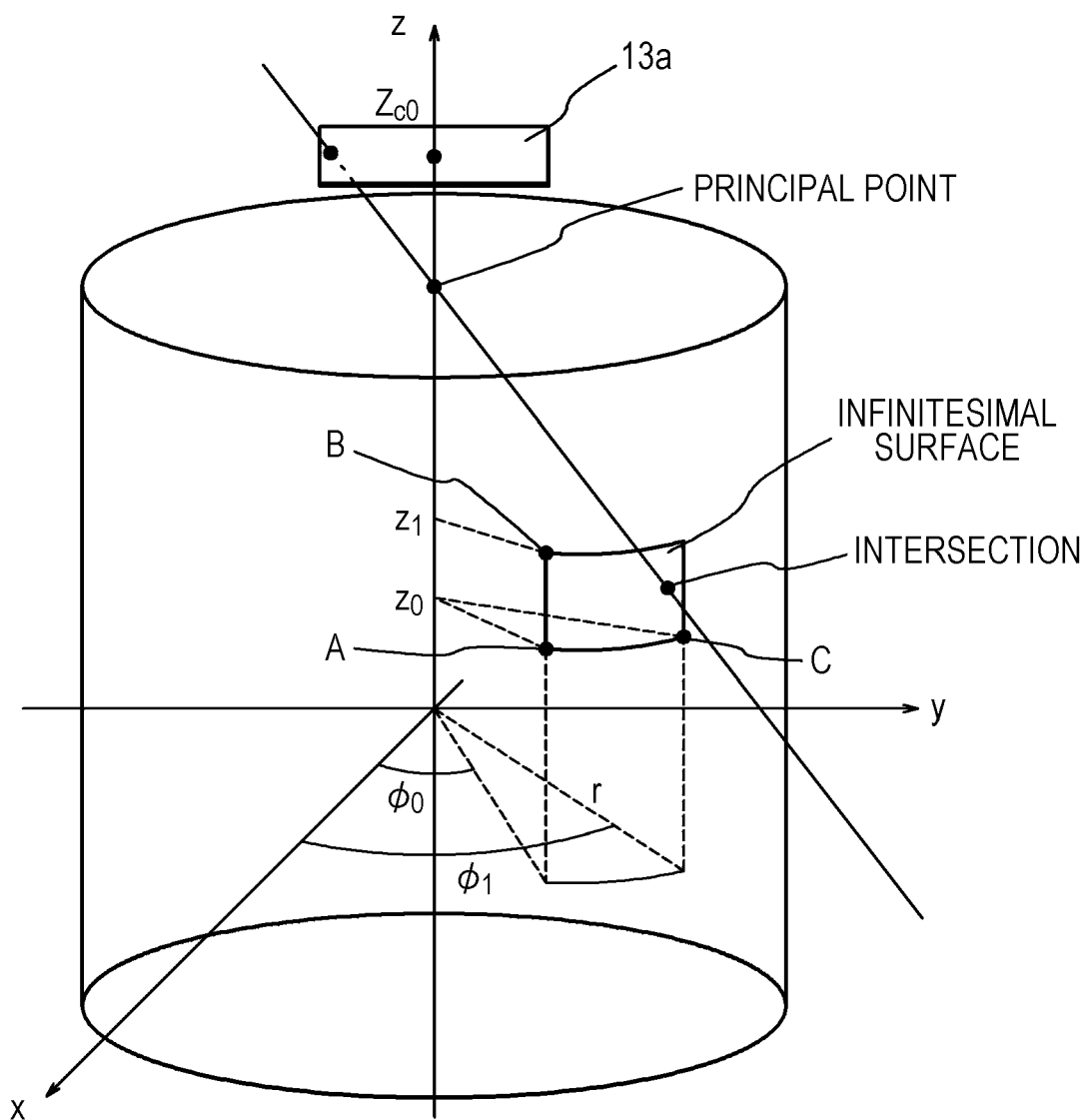
FIG. 5 is a diagram for describing an intersection between a cylindrical surface in the cylindrical coordinates and the straight line illustrated in FIGS. 4A and 4B.

In the present embodiment, the intersection between the cylindrical surface and the straight line is calculated with the center of the light receiving element 13a being on the z-axis as illustrated in FIG. 5. According to the formula (Formula 4) and the formula (Formula 6), the intersection between the cylindrical surface and the straight line can be represented as in the following formula (Formula 8)

$$a_{x1}s_1 + a_{x2}s_2 + s_{x0} = a_x l + l_{x0}$$

$$a_{y1}s_1 + a_{y2}s_2 + s_{y0} = a_y l + l_{y0}$$

$$a_{z1}s_1 + a_{z2}s_2 + s_{z0} = a_z l + l_{z0} \quad \text{[Formula 8]}$$

The parameters $a_{x1}$, $a_{x2}$, $s_{x0}$, $a_{y1}$, $a_{y2}$, $s_{y0}$, $a_{z1}$, $a_{z2}$, $s_{z0}$ for the cylindrical surface are known from the formula (Formula 5). Moreover, the parameters $a_x$, $l_{x0}$, $a_y$, $l_{y0}$, $a_z$, $l_{z0}$ for the straight line are known from the formula (Formula 7). Using these parameters, it can be said that the above-described formula (Formula 8) is the system of linear simultaneous equations with three unknowns using $s_1$, $s_2$, 1 as variables. Thus, the values of $s_1$, $s_2$, and 1 are determined. The values of $s_1$ and $s_2$ obtained as described above are substituted into the formula (Formula 4), or the value of 1 is substituted into the formula (Formula 6). In this manner, the intersection between the cylindrical surface and the straight line can be derived. Note that a case where the infinitesimal surface is farther than the principal point as viewed from the light receiving element 13a, i.e., the case of l>1, has a probability that light from the infinitesimal surface exist on the cylindrical surface enters the light receiving element 13a.

Figure 6A:
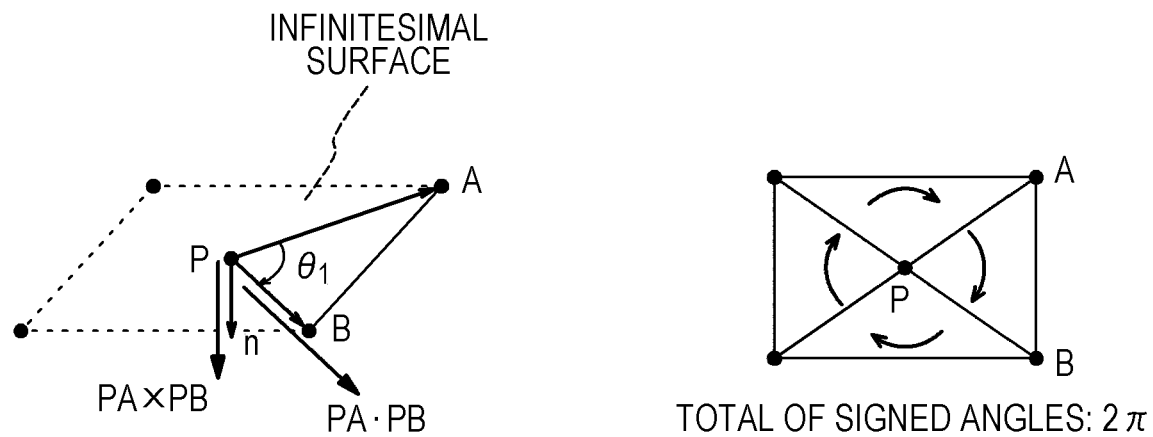
FIGS. 6A and 6B are diagrams for describing the method for determining whether or not the intersection illustrated in FIG. 5 is inside an infinitesimal surface.
Figure 6B:
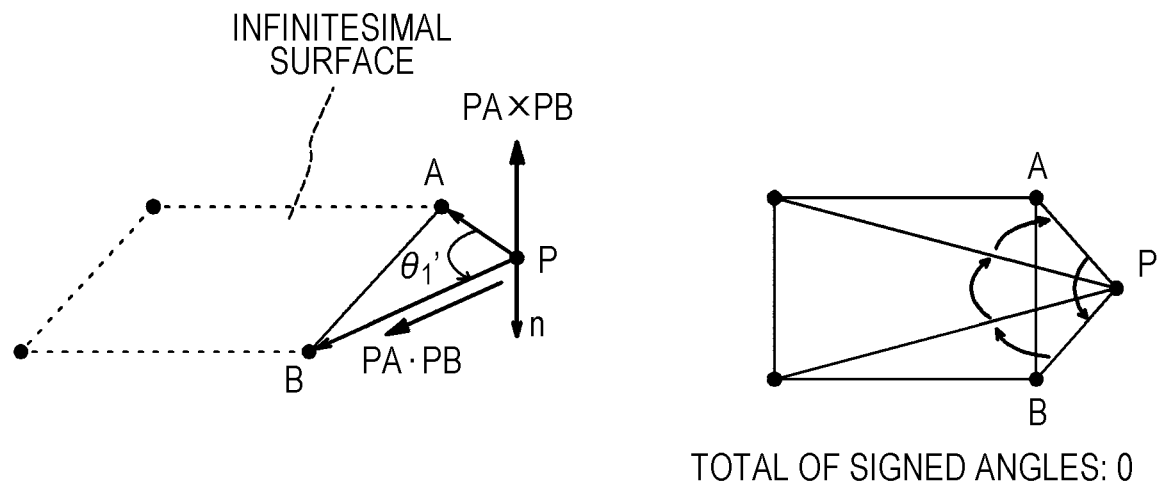

For the derived intersection hereinafter referred to as a "determination point P," it is determined whether or not the determination point P is inside the infinitesimal surface. FIGS. 6A and 6B illustrate such a determination method. In the determination method, both the determination point P and a pair of two vertices A, B adjacent to each other in the infinitesimal surface are focused. FIG. 6A illustrates, as an example, a state in which the determination point P is inside the infinitesimal surface. Moreover, FIG. 6B illustrates, as an example, a state in which the determination point P is outside the infinitesimal surface. Note that both a PA vector and a PB vector respectively illustrated in each of FIGS. 6A and 6B is a vector of the relative positions of two points A, B with a reference point as the determination point P. In this case, "n" indicates a normal vector to the surface. Moreover, an angle (a signed angle) θ1 between the PA vector and the PB vector illustrated in FIG. 6A can be represented as in the following formula (Formula 9). In this case, PA·PB is the inner product of the PA vector and the PB vector. PA×PB is the outer product of the PA vector and the PB vector. Moreover, PA×PB n is the inner product of the above-described outer product and the normal vector n. Note that a signed angle θ1' illustrated in FIG. 6B can be also represented by the same formula as the formula (Formula 9).

$$\theta_1 = \tan^{-1} \frac{PA \times PB \cdot n}{PA \cdot PB} \quad \text{[Formula 9]}$$

Calculation of the signed angle is performed for all combinations of adjacent ones of the vertices of the infinitesimal surfaces. In a case where the determination point P is present inside the infinitesimal surface and an inner surface of the infinitesimal surface faces an image capturing device 1 side as viewed from the image capturing device 1, i.e., faces inward, as illustrated in FIG. 6A, the total of four calculated signed angles is $2\pi$ in theory. In a case where the determination point P is inside the infinitesimal surface and an outer surface of the infinitesimal surface faces the image capturing device 1 side, i.e., faces outward, the total of four calculated signed angles is $-2\pi$ in theory. On the other hand, in a case where the determination point P is present outside the infinitesimal surface as illustrated in FIG. 6B, the total of four calculated signed angles is 0 in theory. Note that in the case of calculating the signed angle based on data actually obtained by image capturing by the image capturing device 1, a theoretical value is not sometimes obtained due to, e.g., an error. Thus, in a case where a calculated absolute value is greater than a certain predetermined value such as $\pi$, it is sometimes determined that the determination point P is present inside the infinitesimal surface. Next, in a case where there are multiple infinitesimal surfaces which the determination point P is inside, determination on whether the infinitesimal surface faces inward or outward as viewed from the image capturing device 1 is made in ascending order of 1, i.e., in ascending order of a distance close to the image capturing device 1. In a case where the total of signed angles is a negative value, it is determined as facing outward and it is determined that receiving of reflected light is impossible. In a case where the total of signed angles is a positive value, it is determined as facing inward and it is determined that receiving of reflected light is possible. Such determination is repeated in the ascending order of 1, and in a case where determination as facing outward is made once, it is subsequently determined that receiving of reflected light is impossible, i.e., no image is captured.

When the light receiving element corresponding to each infinitesimal surface is determined as described above, the pixel value corresponding to each infinitesimal surface is determined from a pixel value of the two-dimensional image data. Based on the above-described reference data, the radius $r_P$ of the tubular body in a case where the distance l corresponding to the received pixel value is defined as $l_P$, and the distance between the infinitesimal surface and the principal point is $l_P$ is calculated for each infinitesimal surface. The radius $r_P$ described herein is a distance from a principal point locus to the inner surface in a tubular body section perpendicular to the principal point locus. The radius $r_P$ is calculated for all of extracted infinitesimal surfaces.

For the entire two-dimensional image data, calculation of the radius $r_P$ corresponding to each infinitesimal surface is performed as described above. An image of each infinitesimal surface is captured in multiple two-dimensional image data pieces, and therefore, multiple radiuses $r_P$ corresponding to each infinitesimal surface are calculated. In this case, the average of the radiuses $r_P$ may be taken as the radius $r_P$ of such an infinitesimal surface. The radius $r_P$ of the infinitesimal surface is the distance between each infinitesimal surface and the principal point locus, and therefore, the infinitesimal surfaces are sequentially connected to each other, so that the three-dimensional shape data of the inside of the tubular body can be built.

After it has been determined whether or not the infinitesimal surface is on the straight line and receiving of reflected light from such an infinitesimal surface is allowed, the pixel value of each pixel of the two-dimensional image data is set as the sum of the intensity of reflected light from each infinitesimal surface exist on the straight line as described above. Further, based on this pixel value, the intensity of the reflected light on each infinitesimal surface which exist on the straight line and whose reflected light is receivable is calculated. For example, it is assumed that a pixel value of a certain pixel m is $v_m$. Moreover, it is assumed that the intensity of reflected light from the infinitesimal surface exist on the cylindrical surface at a position n in the cylindrical coordinates is $u_n$. Using a coefficient $a_{mn}$, the above-described infinitesimal surface determined that the infinitesimal surface is on the straight line and the reflected light from the infinitesimal surface is receivable is assumed as $a_{mn} \neq$ such as $a_{mn}=1$. Moreover, the infinitesimal surface determined that the infinitesimal surface does not exist on the above-described straight line is assumed as $a_{mn}=0$. In this case, a relationship between the pixel value $v_m$ of each pixel of the two-dimensional image data and the sum of the intensity un of the reflected light from each infinitesimal surface exist on the straight line can be represented as in the following formula (Formula 10).

$$v_m = \sum_{n=1}^{N} a_{mn} u_n \qquad \text{[Formula 10]}$$

In a case where such a relationship is considered for pixel values v1 to vM of all pixels, a matrix can be represented as in the following formula (Formula 11). M in the formula (Formula 11) indicates the total number of pixels. In the received multiple two-dimensional image data, such a number is the total number of effective pixels of each of the multiple two-dimensional image data pieces. Note that in a certain capturing, if a certain light receiving element has no image capturing surface which can receive reflected light, such a light receiving element is excluded. Further, in all capturing, image capturing surfaces which are not received by any light receiving elements are also excluded.

$$\begin{bmatrix} v_1 \\ v_2 \\ v_3 \\ \vdots \\ v_m \\ \vdots \\ v_M \end{bmatrix} = \begin{bmatrix} a_{11} & a_{12} & a_{13} & \cdots & a_{1n} & \cdots & a_{1N} \\ a_{21} & a_{22} & a_{23} & \cdots & a_{2n} & \cdots & a_{2N} \\ a_{31} & a_{32} & a_{33} & \cdots & a_{3n} & \cdots & a_{3N} \\ \vdots & \vdots & \vdots & \vdots & \vdots & \vdots & \vdots \\ a_{m1} & a_{m2} & a_{m3} & \cdots & a_{mn} & \cdots & a_{mN} \\ \vdots & \vdots & \vdots & \vdots & \vdots & \vdots & \vdots \\ a_{M1} & a_{M2} & a_{M3} & \cdots & a_{Mn} & \cdots & a_{MN} \end{bmatrix} \begin{bmatrix} u_1 \\ u_2 \\ u_3 \\ \vdots \\ u_m \\ \vdots \\ u_N \end{bmatrix} \qquad \text{[Formula 11]}$$

A matrix including $v_1, v_2, \ldots, v_M$ in the formula (Formula 11) is defined as v. Moreover, a matrix including $a_{11}, a_{12}, \ldots, a_{MN}$ is defined as A. Further, a matrix including $u_1, u_2, \ldots, u_N$ is taken as u. In this case, the formula (Formula 11) can be described as v=Au. This formula can be converted in the similar way to the following formula (Formula 12). Thus, the matrix u can be obtained. As described above, based on the formula (Formula 12), the unknown intensity of the reflected light from each infinitesimal surface exist on the straight line can be calculated.

$$v=Au$$

$$A^T v = A^T A u$$

$$(A^T A)^{-1} A^T v = u$$

$$u = (A^T A)^{-1} A^T v \qquad \text{[Formula 12]}$$

Thereafter, the actual tubular body, i.e., the infinitesimal surface inside the external ear canal of a hearing aid user in the case of the present embodiment, is estimated based on distribution of the reflected light intensity of each infinitesimal surface exist on the straight line as described above. Based on the estimated infinitesimal surface, the three-dimensional shape data of the inside of the tubular body is built. For example, in a case where the infinitesimal surfaces exist on the straight line are arranged in the order of a distance from the light receiving element 13a and the distribution of the reflected light intensity is normal distribution, the infinitesimal surface corresponding to the intensity as an extreme can be estimated as the infinitesimal surface inside the actual tubular body. Note that various methods can be selected as the technique of estimating the infinitesimal surface from the distribution of the reflected light intensity. The estimated infinitesimal surfaces are sequentially connected, so that the three-dimensional shape data of the inside of the tubular body can be built.

Note that the above-described cylindrical coordinates have the center axis extending linearly on the line. However, in a case where the image capturing device 1 moves on a curved line or in a case where the movement locus of the principal point of the objective optical system 12 is a curved line, the infinitesimal surface may be set based on curved cylindrical coordinates having the curved line as a center axis. The intensity of the reflected light from the infinitesimal surface varies according to the inner product of a directional vector of the straight line connecting the light receiving element 13a and the principal point of the objective optical system 12 and an inward normal vector of the infinitesimal surface of the curved cylindrical coordinates and a lighting condition. Thus, the reference data and the value of $a_{mn}$ may be determined accordingly.

The present disclosure is not limited to produce the three-dimensional shape data of the inside of the external ear canal. For example, the present disclosure can be applied for reproducing and reappearing of the inner shapes of various tubular bodies, such like, digestive tract such as the intestines and the respiratory tract as human organ, and water pipe as tubing products. Moreover, the present disclosure can be also applied to, for example, automatic identification method of a clinical condition of human body and of damaged portions or defective portions of other tubular bodies.

The three-dimensional shape data production method and the three-dimensional shape data production system according to the present disclosure may be the following first to third three-dimensional shape data production methods or the following first to third three-dimensional shape data production systems.

The first three-dimensional shape data production method is a three-dimensional shape data production method including the step of generating multiple pieces of two-dimensional image data based on a signal from an image capturing device configured to be movable inside a tubular body and configured to capture an image of the inside of the tubular body, the step of receiving space information on the image capturing device upon image capturing based on a signal from a motion sensor, and the step of relating the two-dimensional image data and the space information with each other and generating three-dimensional shape data of the inside of the tubular body based on the two-dimensional image data and the space information.

The second three-dimensional shape data production method is the above-described first three-dimensional shape data production method in which the image capturing device includes an objective optical system and an image capturing element arranged at the position of image formation by the objective optical system and configured to receive reflected light from the inside of the tubular body and the step of generating the three-dimensional shape data includes the step of calculating a movement locus of a principal point of the objective optical system in association with movement of the image capturing device based on the space information to set cylindrical coordinates about the movement locus as a center axis and discretizing a surrounding space of the image capturing device based on the cylindrical coordinates to set multiple infinitesimal surfaces, which form the surrounding space, according to the cylindrical coordinates, the step of setting a straight line connecting each light receiving element of the image capturing element and the principal point, the step of determining whether or not the infinitesimal surfaces exist on the straight line, the step of determining whether or not reflected light from the infinitesimal surfaces can enter each light receiving element of the image capturing element, the step of setting a pixel value of each pixel of the two-dimensional image data as the sum of the intensity of the reflected light from each infinitesimal surface which exist on the straight line and whose light can enter each light receiving element and calculating the intensity of the reflected light on each infinitesimal surface exist on the straight line based on the pixel value, and the step of estimating the infinitesimal surfaces inside an actual tubular body based on distribution of the reflected light intensity of each infinitesimal surface exist on the straight line and building three-dimensional shape data of the inside of the tubular body based on the estimated infinitesimal surfaces.

The third three-dimensional shape data production method is the first or second three-dimensional shape data production method further comprising the step of correcting the space information on the image capturing device as obtained by the motion sensor based on space information on the tubular body upon image capturing, the space information on the tubular body being obtained by other motion sensors.

The first three-dimensional shape data production system is a first three-dimensional shape data production system including a two-dimensional image data generator configured to generate multiple pieces of two-dimensional image data based on a signal from an image capturing device configured to be movable inside a tubular body and configured to capture an image of the inside of the tubular body, a space information receiver configured to receive space information on the image capturing device upon image capturing based on a signal from a motion sensor, and a three-dimensional shape data generator configured to relate the two-dimensional image data and the space information with each other and generate three-dimensional shape data of the inside of the tubular body based on the two-dimensional image data and the space information.

The second three-dimensional shape data production system is the first three-dimensional shape data production system in which the image capturing device includes a tip end portion having an objective optical system into which reflected light from the inside of the tubular body enters and a bent portion supporting the tip end portion and provided bendably and the motion sensor is provided at the tip end portion.

The third three-dimensional shape data production system is the first or second three-dimensional shape data production system further including a holding device configured to directly or indirectly hold the tubular body.

The invention claimed is:
1. A three-dimensional shape data production method comprising:
    a step of generating multiple pieces of two-dimensional image data based on a signal from an image capturing device configured to be movable inside a tubular body and configured to capture an image of the inside of the tubular body, the image capturing device including a lighting, an objective optical system, and an image capturing element having M light receiving elements, M being a positive integer equal to or greater than two, arranged at a position of image formation by the objective optical system and configured to receive reflected light from the inside of the tubular body which radiates at the lighting, the two-dimensional image data including M pixel values, each of the M pixel values being generated by a respective one of the M light receiving elements;
    a step of receiving space information on the image capturing device upon image capturing by the image capturing device based on a signal from a motion sensor placed at the image capturing device; and
    a step of relating the two-dimensional image data and the space information with each other and generating three-dimensional shape data of the inside of the tubular body based on the two-dimensional image data and the space information, wherein
    the step of generating the three-dimensional shape data includes:
        calculating a movement locus of a principal point of the objective optical system in association with movement of the image capturing device based on the space information to determine cylindrical coordinates about the movement locus as a center axis;
        discretizing, in the cylindrical coordinates, a space surrounding the image capturing device into N infinitesimal surfaces, N being a positive integer equal to or greater than two;
        determining M straight lines in the cylindrical coordinates, each of the M straight lines passing through the principal point and a respective one of the M light receiving elements;
        calculating, using formula $u=(A^T A)^{-1} A^T v$, N reflected light intensity values, each of the N reflected light intensity values indicating intensity of light reflected from a respective one of the N infinitesimal surfaces; and
        estimating infinitesimal surfaces which forms the inside of the tubular body based on distribution of the N reflected light intensity values and building three-dimensional shape data of the inside of the tubular body based on the estimated infinitesimal surfaces, wherein
            in the formula, the matrix A has M rows and N columns and includes elements $a_{mn}$ ($1 \le m \le M$, $1 \le n \le N$),
            each of the elements $a_{mn}$ meeting a first condition has a value other than zero, and each of the elements $a_{mn}$ meeting a second condition has a value of zero, the first condition requiring that one of the N infinitesimal surfaces identified by the positive integer n exists on one of the M straight lines passing through one of the M light receiving elements identified by the positive integer m and reflected light from the one of the N infinitesimal surfaces identified by the positive integer n is receivable for the one of the M light receiving elements identified by the positive integer m, the second condition requiring that the one of the N infinitesimal surfaces identified by the positive integer n does not exist on the one of the M straight lines passing through the one of the M light receiving elements identified by the positive integer m, the matrix v has M rows and one columns, and includes elements $v_m$ the elements $v_m$ each representing one of the M pixel values generated by the one of the M light receiving elements identified by the positive integer m, and the matrix u has N rows and one column, and includes elements $u_n$, the elements $u_n$ each representing one of the N reflected light intensity values related to one of the N infinitesimal surfaces identified by the positive integer n.

2. The three-dimensional shape data production method according to claim 1, further comprising:

a step of correcting the space information on the image capturing device as obtained by the motion sensor based on the space information on the tubular body upon image capturing, the space information on the tubular body being obtained by other motion sensors.

3. A three-dimensional shape data production system comprising:

a two-dimensional image data generation device configured to generate multiple pieces of two-dimensional image data based on a signal from an image capturing device configured to be movable inside a tubular body and configured to capture an image of the inside of the tubular body, the image capturing device including a lighting, an objective optical system, and an image capturing element having M light receiving elements, M being a positive integer equal to or greater than two, arranged at a position of image formation by the objective optical system and configured to receive reflected light from the inside of the tubular body which radiates at the lighting, the two-dimensional image data including M pixel values, each of the M pixel values being generated by a respective one of the M light receiving elements;

a space information receiving device configured to receive space information on the image capturing device upon image capturing based on a signal from a motion sensor placed at the image capturing device; and a three-dimensional shape data generation device configured to relate the two-dimensional image data and the space information with each other and generate three-dimensional shape data of the inside of the tubular body based on the two-dimensional image data and the space information, wherein to generate the three-dimensional shape data, the three-dimensional shape data generation device:

calculates a movement locus of a principal point of the objective optical system in association with movement of the image capturing device based on the space information to determine cylindrical coordinates about the movement locus as a center axis;

discretizes, in the cylindrical coordinates, a space surrounding the image capturing device into N infinitesimal surfaces, N being a positive integer equal to or greater than two;

determines M straight lines in the cylindrical coordinates, each of the M straight lines passing through the principal point and a respective one of the M light receiving elements;

calculates, using formula $u=(A^T A)^{-1}A^T v$, N reflected light intensity values, each of the N reflected light intensity values indicating intensity of light reflected from a respective one of the N infinitesimal surfaces; and estimates infinitesimal surfaces which forms the inside of the tubular body based on distribution of the N reflected light intensity values and building three-dimensional shape data of the inside of the tubular body based on the estimated infinitesimal surfaces, wherein in the formula, the matrix A has M rows and N columns and includes elements $a_{mn}$ ($1 \leq m \leq M$, $1 \leq n \leq N$), each of the elements $a_{mn}$ meeting a first condition has a value other than zero, and each of the elements $a_{mn}$ meeting a second condition has a value of zero, the first condition requiring that one of the N infinitesimal surfaces identified by the positive integer n exists on one of the M straight lines passing through one of the M light receiving elements identified by the positive integer m and reflected light from the one of the N infinitesimal surfaces identified by the positive integer n is receivable for the one of the M light receiving elements identified by the positive integer m, the second condition requiring that the one of the N infinitesimal surfaces identified by the positive integer n does not exist on the one of the M straight lines passing through the one of the M light receiving elements identified by the positive integer m, the matrix v has M rows and one columns, and includes elements $v_m$ the elements $v_m$ each representing one of the M pixel values generated by the one of the M light receiving elements identified by the positive integer m, and the matrix u has N rows and one column, and includes elements $u_n$, the elements $u_n$ each representing one of the N reflected light intensity values related to one of the N infinitesimal surfaces identified by the positive integer n.

4. The three-dimensional shape data production system according to claim 3, wherein the image capturing device further includes a tip end portion having the objective optical system into which reflected light from the inside of the tubular body which radiates at the lighting enters, and a bent portion supporting the tip end portion and provided bendably wherein the motion sensor is provided at the tip end portion.

5. The three-dimensional shape data production system according to claim 3, further comprising:

a holding device configured to directly or indirectly hold the tubular body.

* * * * *